United States Patent
Chubb et al.

(10) Patent No.: US 9,226,928 B2
(45) Date of Patent: *Jan. 5, 2016

(54) SPIROCYCLIC ISOXAZOLINE PARASITICIDAL COMBINATIONS

(71) Applicant: Zoetis Services LLC, Florham Park, NJ (US)

(72) Inventors: Nathan Anthony Logan Chubb, Kalamazoo, MI (US); Kevin Evans, Florham Park, NJ (US); Tom L. McTier, Kalamazoo, MI (US); Patrick F. M. Meeus, Parkville (AU)

(73) Assignee: Zoetis Services LLC, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/426,264

(22) PCT Filed: Sep. 4, 2013

(86) PCT No.: PCT/US2013/057925
§ 371 (c)(1),
(2) Date: Mar. 5, 2015

(87) PCT Pub. No.: WO2014/039475
PCT Pub. Date: Mar. 13, 2014

(65) Prior Publication Data
US 2015/0209355 A1   Jul. 30, 2015

Related U.S. Application Data

(60) Provisional application No. 61/698,116, filed on Sep. 7, 2012.

(51) Int. Cl.
| | |
|---|---|
| A61K 31/506 | (2006.01) |
| A61K 31/365 | (2006.01) |
| A61K 31/422 | (2006.01) |
| A01N 43/90 | (2006.01) |
| A61K 31/505 | (2006.01) |

(52) U.S. Cl.
CPC .............. *A61K 31/506* (2013.01); *A01N 43/90* (2013.01); *A61K 31/365* (2013.01); *A61K 31/422* (2013.01); *A61K 31/505* (2013.01)

(58) Field of Classification Search
None
See application file for complete search history.

(56) References Cited

U.S. PATENT DOCUMENTS

| 8,415,310 | B2 | 4/2013 | Vaillancourt et al. |
| 8,466,115 | B2 * | 6/2013 | Curtis ............... A01N 43/90 |
| | | | 514/210.18 |
| 2012/0035122 | A1 | 2/2012 | Vaillancourt et al. |
| 2015/0183795 | A1 | 7/2015 | Billen |

FOREIGN PATENT DOCUMENTS

| WO | 2012/060317 | 5/2012 |
| WO | 2012/120399 | 9/2012 |

OTHER PUBLICATIONS

PCT International Search Report, PCT/US2013/057925 filed Sep. 4, 2013 (3 pages).

* cited by examiner

*Primary Examiner* — Kamal Saeed
(74) *Attorney, Agent, or Firm* — Paul M. Misiak; Barbara L. Renda

(57) ABSTRACT

The present invention relates to a novel antiparasitic composition comprising an effective amount of a) a Formula (1) compound, wherein $R^{1a}$, $R^{1b}$, $R^{1c}$, $R^2$, $R^3$, $R^4$, and n are as defined herein, stereoisomer thereof, or a pharmaceutical or veterinary acceptable salt thereof, b) a macrocyclic lactone or derivative thereof and c) optionally, at least one additional veterinary agent, and further comprising at least one veterinary or pharmaceutical acceptable carrier; and a method of treating an animal with a parasitic infection, by administering an effective amount of said composition to the animal in need thereof.

(1)

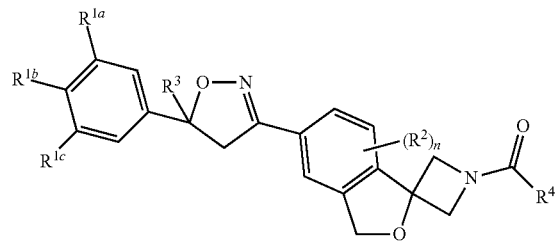

20 Claims, No Drawings

SPIROCYCLIC ISOXAZOLINE PARASITICIDAL COMBINATIONS

CROSS-REFERENCE TO RELATED APPLICATIONS

This application is a 371 filing of International Application No. PCT/US2013/057925 filed Sep. 4, 2013, which claims the benefit of U.S. Provisional Application 61/698,116 filed Sep. 7, 2012.

FIELD OF INVENTION

The present invention relates to a novel antiparasitic composition comprising a) a Formula (1) compound, Formula (1.1) compound, or Compound A, b) a macrocyclic lactone or derivative thereof, and optionally, c) at least one additional veterinary agent; compositions thereof, and a method of treating an animal with a parasitic infection with said composition.

BACKGROUND OF THE INVENTION

The Formula (1) compounds were previously shown to be potent antiparasiticides. The Formula (1) compounds and Formula (1.1) compound, preparation, compositions, and methods of use are described in WO2012/120399. The (S)-enantiomer of the Formula (1.1) compound is herein referred to as Compound A. Additionally, the crystal form of Compound A (Form A) was described in PCT/US2013/56945. Compound A is also referred to as (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone).

The object of the invention is, in particular, to use known parasiticides in order to prepare a composition which is highly effective against both endoparasites and ectoparasites. In many instances, parasiticidal combinations are used as a means of broadening the scope of efficacy on different parasites, generally endoparasites or ectoparasites, including those that may be showing resistance to a single agent. In some cases, the combination provides an unexpected scope of activity against the parasite that would not have been anticipated by the addition of another veterinary agent (i.e., a synergistic effect).

SUMMARY OF THE INVENTION

The present invention relates to a novel antiparasitic composition comprising a) a Formula (1) compound, stereoisomer thereof, or a pharmaceutical or veterinary acceptable salt thereof, b) a macrocyclic lactone or derivative thereof, and optionally, c) at least one additional veterinary agent

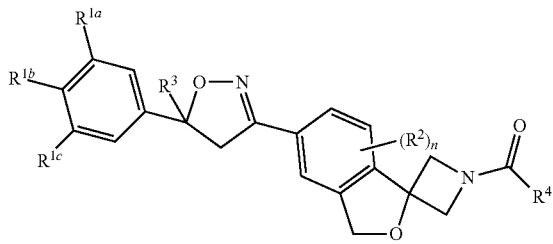

(1)

wherein $R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)NH$_2$, —SF$_5$, or —S(O)$_p$R;

$R^2$ is fluoro, chloro, or $C_1$-$C_6$alkyl;

$R^3$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl $R^4$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

when $R^4$ is $C_1$-$C_6$alkyl or $C_0$-$C_6$alkyl$C_3$-$C_6$cycloalkyl, then each moiety can be optionally substituted by at least one substituent selected from cyano, halo, hydroxyl, oxo, $C_1$-$C_6$alkoxy, $C_1$-$C_6$haloalkoxy, $C_1$-$C_6$haloalkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$;

when $R^4$ is $C_0$-$C_6$alkylphenyl, $C_0$-$C_6$alkylheteroaryl, or $C_0$-$C_6$alkylheterocycle, then each moiety can be further optionally substituted with at least one substituent selected from cyano, halo, oxo, =S, =NR$^5$, hydroxyl$C_1$-$C_6$alkyl-, hydroxyl, $C_1$-$C_6$alkoxy, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

stereoisomers thereof, or a pharmaceutical or veterinary acceptable salt thereof.

In yet another aspect of the invention, each of $R^{1a}$, $R^{1b}$, and $R^{1c}$ are independently selected from hydrogen, halo, cyano, $C_1$-$C_6$ haloalkyl, and $C_0$-$C_3$alkyl$C_3$-$C_6$ cycloalkyl. In yet another aspect of the invention, each of $R^{1a}$, $R^{1b}$, and $R^{1c}$ are independently selected from hydrogen, halo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$ haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl. In yet another aspect of the invention, each of $R^{1a}$, $R^{1b}$, and $R^{1c}$ are independently selected from hydrogen, fluoro, chloro, bromo, and —CF$_3$. In yet another aspect of the invention, each of $R^{1a}$, $R^{1b}$, and $R^{1c}$ are independently selected from hydrogen, fluoro, chloro, and —CF$_3$. In yet another aspect of the invention, each of $R^{1a}$, $R^{1b}$, and $R^{1c}$ are independently selected from hydrogen, fluoro, and chloro. In yet another aspect of the invention, each of $R^{1a}$, $R^{1b}$, and $R^{1c}$ are chloro. In yet another aspect of the invention, each of $R^{1a}$ and $R^{1c}$ are chloro and $R^{1b}$ is hydrogen. In yet another aspect of the invention, each of $R^{1a}$ and $R^{1c}$ are chloro and $R^{1b}$ is fluoro.

In yet another aspect of the invention, $R^2$ is halo, cyano, $C_1$-$C_6$alkyl, $C_1$-$C_6$haloalkyl, hydroxyl, —C(O)NR$^a$R$^b$, —S(O)$_p$R, or —OR. In yet another aspect of the invention, $R^2$ is halo, cyano, $C_1$-$C_6$alkyl, $C_1$-$C_6$haloalkyl, or hydroxyl. In yet another aspect of the invention, $R^2$ is fluoro, chloro, bromo, cyano, methyl, ethyl, $CF_3$, or hydroxyl. In yet another aspect of the invention, $R^2$ is fluoro, chloro, cyano, methyl, ethyl, or $CF_3$.

In yet another aspect of the invention, $R^3$ is cyano, $C_1$-$C_6$alkyl, $C_1$-$C_6$haloalkyl, or —C(O)NH$_2$. In yet another aspect of the invention, $R^3$ is cyano, $C_1$-$C_6$alkyl, or $C_1$-$C_6$haloalkyl. In yet another aspect of the invention, $R^3$ is cyano, methyl, ethyl, or $C_1$-$C_6$haloalkyl. In yet another aspect of the invention, $R^3$ is cyano, methyl, or $C_1$-$C_6$haloalkyl. In yet another aspect of the invention, $R^3$ is cyano or $C_1$-$C_6$haloalkyl. In yet another aspect of the invention, $R^3$ is $C_1$-$C_6$haloalkyl. In yet another aspect of the invention, $R^3$ is —$CF_3$, —$CHF_2$, —$CH_2F$, and —$CF_2Cl$. In yet another aspect of the invention, $R^3$ is —$CF_3$, —$CHF_2$, and —$CH_2F$. In yet another aspect of the invention, $R^3$ is —$CF_3$.

In yet another aspect of the invention, $R^4$ is $C_1$-$C_6$alkyl, $C_0$-$C_6$alkylphenyl, $C_0$-$C_6$alkyl$C_3$-$C_6$cycloalkyl, $C_0$-$C_6$alkylheteroaryl, or $C_0$-$C_6$alkyl heterocycle. In yet another aspect of the invention, $R^4$ is $C_1$-$C_6$alkyl. In yet another aspect of the invention, $R^4$ is methyl, ethyl, propyl, isopropyl, t-butyl, isobutyl, and the like. Each of the $R^4$ $C_1$-$C_6$alkyls can be optionally substituted as defined herein, for example, with at least one substituent selected from cyano, hydroxyl, halo, trifluoromethyl, —S(O)$_p$R$^c$, and —NHCHO. In yet another aspect of the invention, $R^4$ is $C_0$-$C_6$alkyl$C_3$-$C_6$cycloalkyl. In yet another aspect of the invention, $R^4$ is cyclopropyl, cyclobutyl, cyclopentyl, —CH$_2$cyclopropyl, —CH$_2$cyclobutyl, —CH$_2$cyclopentyl, thiatane, oxetane, azetidine, —(CH$_2$)$_2$cyclopropyl, —(CH$_2$)$_2$cyclobutyl, —(CH$_2$)$_2$cyclopentyl, —CH$_2$thiatane, —CH$_2$oxetane, —CH$_2$azetidine, tetrahydrofuran, tetrahydrothiophene, pyrrolidine, and the like. Each of the $R^4$ $C_0$-$C_6$alkyl$C_3$-$C_6$cycloalkyls can be optionally substituted as defined herein, for example, with at least one substituent selected from cyano, oxo, —S(O)$_p$R$^c$, hydroxyl, —CH$_2$OH, halo, methyl, ethyl, and trifluoromethyl. In yet another aspect of the invention, $R^4$ is $C_0$-$C_6$alkylphenyl. In yet another aspect of the invention, $R^4$ is phenyl, —CH$_2$phenyl, —(CH$_2$)$_2$phenyl, and the like. In yet another aspect of the invention, the $R^4$ $C_0$-$C_6$alkylphenyl moieties can be optionally substituted as defined herein, for example, cyano, hydroxyl, —S(O)$_p$R$^c$, methyl, halo, and trifluoromethyl. In yet another aspect of the invention, $R^4$ is $C_0$-$C_6$alkylheteroaryl. In yet another aspect of the invention, $R^4$ is pyrazole, imidazole, pyridine, —CH$_2$pyrazole, —CH$_2$pyridine, —CH$_2$imidazole, —(CH$_2$)$_2$ pyrazole, —(CH$_2$)$_2$pyridine, and —(CH$_2$)$_2$imidazole. Each of the $R^4$ $C_0$-$C_6$alkylheteroaryl moieties can be optionally substituted as defined herein, for example, with at least one substituent selected from cyano, hydroxyl, —S(O)$_p$ R$^c$, methyl, halo, and trifluoromethyl. In yet another aspect of the invention, $R^4$ is $C_0$-$C_6$alkylheterocycle. In yet another aspect of the invention, $R^4$ is oxirane, thiarane, aziridine, oxetane, azetidine, thiatane, tetrahydrofuran, tetrahydrothiophene, pyrrolidine, tetrahydropyrane, piperidine, piperazine, —CH$_2$oxirane, —CH$_2$thiarane, —CH$_2$aziridine, —CH$_2$oxetane, —CH$_2$azetidine, —CH$_2$thiatane, —CH$_2$tetrahydrofuran, —CH$_2$tetrahydrothiophene, —CH$_2$pyrrolidine, —CH$_2$tetrahydropyrane, —CH$_2$piperidine, —CH$_2$piperazine, and the like. Each of the $R^4$ $C_0$-$C_6$alkylheterocyclic moieties can be optionally substituted as defined herein, for example, with at least one substituent selected from hydroxyl, —S(O)$_p$R$^c$, cyano, methyl, halo, and trifluoromethyl.

In another aspect of the invention, the integer n of $(R^2)_n$ is 0. In another aspect of the invention, the integer n of $(R^2)_n$ is 1. When the integer n is 1, then $R^2$ is as defined herein. In yet another aspect of the invention, the integer n of $(R^2)_n$ is 2. When the integer n is 2, then each $R^2$ is independent of each other and are as described herein.

In yet another aspect of the invention, p is the integer 0. In yet another aspect of the invention, p is the integer 1. In yet another aspect of the invention, p is the integer 2.

In another aspect of the invention, is a composition comprising a Formula (1) compound, stereoisomer thereof, or a pharmaceutical or veterinary acceptable salt thereof, b) a macrocyclic lactone or derivative thereof, and c) at least one additional veterinary agent.

In another aspect of the invention, the Formula (1) compound is selected from the group consisting of:

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Formula 1.1);

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Compound A);

(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone; and (S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, or a stereoisomer thereof, or a pharmaceutical or veterinary acceptable salt thereof.

In another aspect of the invention, the Formula (1) compound is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, hereinafter Formula (1.1),

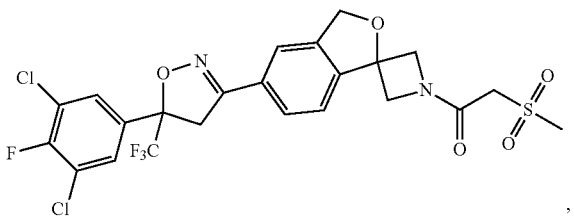

(1.1)

stereoisomers thereof, or a pharmaceutical or veterinary acceptable salt thereof.

In another aspect of the invention, the Formula (1) compound is (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Compound A), or a veterinary or pharmaceutical acceptable salt thereof.

Each of the aforementioned and/or subsequent compositions optionally includes at least one pharmaceutical or veterinary acceptable carrier. Further, each of the aforementioned and/or subsequent compositions includes at least one pharmaceutical or veterinary acceptable carrier.

The invention also contemplates a veterinary or pharmaceutical composition comprising a) a Formula (1.1) compound, b) a macrocyclic lactone or derivative thereof, and optionally, c) at least one additional veterinary agent.

The invention also contemplates a veterinary or pharmaceutical composition comprising a) a Formula (1.1) compound, b) a macrocyclic lactone or derivative thereof, and c) at least one additional veterinary agent.

The invention also contemplates a veterinary or pharmaceutical composition comprising a) Compound A, b) a macrocyclic lactone or derivative thereof, and optionally, c) at least one additional veterinary agent.

The invention also contemplates a veterinary or pharmaceutical composition comprising a) Compound A, b) a macrocyclic lactone or derivative thereof, and c) at least one additional veterinary agent.

The invention also contemplates a veterinary or pharmaceutical composition comprising a) Compound A, b) moxidectin, and optionally, c) at least one additional veterinary agent.

The invention also contemplates a veterinary or pharmaceutical composition comprising a) Compound A, b) moxidectin, and c) at least one additional veterinary agent.

The invention also contemplates a veterinary or pharmaceutical composition comprising a) Compound A, b) moxidectin, and c) pyrantel pamoate, oxantel, morantel, novaluron, imidacloprid, febantel, piperazine citrate, niclosamide, lufenuron, nitenpyram, oxibendazole, fenbendazole, fipronil, and amitraz, or any combination thereof.

The invention also contemplates a veterinary or pharmaceutical composition comprising a) Compound A, b) moxidectin, and c) pyrantel pamoate.

The invention also contemplates a veterinary or pharmaceutical composition comprising a) Compound A, b) selamectin, and optionally, c) at least one additional veterinary agent.

The invention also contemplates a veterinary or pharmaceutical composition comprising a) Compound A, b) milbemycin or milbemycin oxime, and optionally, c) at least one additional veterinary agent.

The invention also contemplates a veterinary or pharmaceutical composition comprising a) Compound A, b) moxidectin, selamectin, milbemycin or milbemycin oxime, and optionally, c) praziquantel or epsiprantel.

The invention also contemplates a veterinary or pharmaceutical composition comprising effective amounts of a Formula (1) compound, Formula (1.1) compound, or Compound A, macrocyclic lactone or derivative thereof, and least one additional veterinary agent.

The invention also contemplates a method of treating a parasitic infection or infestation in an animal, in need thereof, comprising administering a veterinary or pharmaceutical composition comprising a) a Formula (1) compound, Formula (1.1) compound, or Compound A, b) a macrocyclic lactone or derivative thereof, and optionally, c) at least one additional veterinary agent.

The invention also contemplates a method of treating a parasitic infection or infestation in an animal, in need thereof, comprising administering a veterinary or pharmaceutical composition comprising a) Compound A, b) moxidectin, milbemycin, milbemycin oxime, or selamectin, and optionally, c) at least one additional veterinary agent.

The invention also contemplates a method of treating a parasitic infection or infestation in an animal, in need thereof, comprising administering a veterinary or pharmaceutical composition comprising a) Compound A, b) moxidectin, milbemycin, milbemycin oxime, or selamectin, and c) at least one additional veterinary agent.

The invention also contemplates a veterinary or pharmaceutical composition comprising effective amounts of a) a Formula (1), Formula (1.1) compound, or Compound A, b) a macrocyclic lactone or derivative thereof, and optionally, c) at least one additional veterinary agent, as a medicament.

The invention also contemplates the use of the veterinary or pharmaceutical composition comprising a) a Formula (1), Formula (1.1), or Compound A, b) a macrocyclic lactone or derivative thereof, and optionally, c) at least one additional veterinary agent, for the treatment of a parasitic infection or infestation in an animal, in need thereof, by administering an effective amount of each active agent to an animal in need thereof.

In another aspect of the invention, the macrocyclic lactone, or derivative thereof, is selected from the group consisting of: ivermectin, emamectin, selamectin, doramectin, moxidectin, abamectin, eprinomectin, milbemycin, and milbemycine oxime.

In another aspect of the invention, the additional veterinary agent is selected from the group consisting of: monepantel, tetrahydropyrimidines (e.g., pyrantel (pamoate, embonate, citrate, and tartrate salts), oxantel, morantel, and the like), febantel, piperazine citrate, niclosamide, fenbendazole, oxibendazole, mebendazole, flubendazole, dichlorvos, imidacloprid, an insect growth regulator (e.g., s-methoprene, hydroprene, praziquantel, epsiprantel, azadirachtin, diofenolan, fenoxycarb, kinoprene, and the like), chitin synthesis inhibitors (e.g., chlorfluazuron, cryomazine, diflubenzuron, fluazuron, flucycloxuron, flufenoxuron, hexaflumuron, lufenuron, tebufonozide, novaluron, teflubenzuron, triflumuron, and the like), and nitenpyram.

In another aspect of the invention, the veterinary or pharmaceutical composition comprising a) a Formula (1) compound, Formula (1.1) compound, or Compound A, b) a macrocyclic lactone or derivative thereof, and optionally, c) at least one additional veterinary agent is administered to an animal in need thereof by oral, topical, or injectable (subcutaneous, intramuscularly, and intravenously) routes of administration. Preferred routes of administration are oral and topical.

DETAILED DESCRIPTION

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —$OCH_3$, —$OCH_2CH_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "($C_1$-$C_6$)alkyl" refers to a monovalent, straight or branched aliphatic group containing 1 to 6 carbon atoms. Non-exclusive examples of ($C_1$-$C_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: $C_1$alkylphenyl is —$CH_2$phenyl, $C_2$alkylphenyl is —$CH_2CH_2$phenyl, $C_0$phenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═$CH_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl.

"Carbocyclic", as used herein, unless otherwise indicated, refers to a partially saturated or saturated 5- to 7-membered ring containing only carbon atoms and can be monocyclic or part of a fused ring or spiro ring moiety. Examples of carbocyclic rings include cyclopentane, cyclohexane, and cycloheptane. The carbocyclic ring is optionally substituted as described herein.

"Chiral", as used herein, unless otherwise indicated, refers to the structural characteristic of a molecule that makes it impossible to superimpose it on its mirror image, (e.g., "R" and "S" enantiomers). The term is also depicted as an asterisk (i.e., *) in the Examples and preparations and refers to a chiral center which includes both the S and R enantiomers. Unless otherwise stated, a compound structure that does not indicate a particular conformation is intended to encompass compositions of all the possible conformational isomers.

"Composition of the present invention", as used herein, unless otherwise indicated, refers to a composition comprising a) a Formula (1) compound, stereoisomer thereof, or a pharmaceutical or veterinary acceptable salt thereof; Formula (1.1) compound, stereoisomer thereof, or a pharmaceutical or veterinary acceptable salt thereof; or Compound A, or a pharmaceutical or veterinary acceptable salt thereof; including the free base of each respective compound, b) a macrocyclic lactone or derivative thereof, and optionally, c) at least one additional veterinary agent. The composition further comprises at least one pharmaceutical or veterinary acceptable carrier.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of $C_0$-$C_6$alkyl$C_3$-$C_6$cycloalkyl include, methylcyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. $C_0$alkyl$C_3$-$C_6$cycloalkyl is $C_3$-$C_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like. The term "haloalkenyl is defined analogously to the term "haloalkyl" except that the aliphatic chain contains at least one carbon-carbon double bond. Examples of "haloalkenyl" include $CF_3C$=$C$—, $CCl_3C$=$C$—, $HCF_2C$=$C$— and $CF_3C$=$CC$—, and the like. The term "haloalkynyl" is defined analogously to the term "haloalkyl" except that the aliphatic chain contains at least one carbon-carbon triple bond. Examples of "haloalkynyl" include $F_3CC$≡$C$—, $Cl_3CC$≡$C$—, $HF_2CC$≡$C$—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —$CH_2$heteroaryl, $C_2$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —$CH_2$heterocycle, $C_0$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitoes, biting flies (stable fly, horn fly, blow fly, horse fly, and the like), bed bugs, and lice. Preferred compounds of the present invention can be used for the treatment of parasites, i.e., treatment of a parasitic infection or infestation.

"Therapeutically effective amount", or "effective amount" as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "pharmaceutical" acceptable has the same meaning as that recited for "veterinary" acceptable.

When referring to compounds of Formula (1) and Formula (1.1), these compounds also include stereoisomers thereof, and any pharmaceutical or veterinary acceptable salt thereof, while also including the free base.

When referring to Compound A, this compound also includes any pharmaceutical or veterinary acceptable salt thereof, while also including the freebase, and in particular, crystal Form A.

Pharmaceutical/Veterinary Compositions

The composition of the present invention can be administered by any suitable route, preferably in the form of a pharmaceutical acceptable or veterinary acceptable composition adapted to such a route, and in a dose effective amount for the treatment intended. Accordingly, the invention specifically comprises a pharmaceutical or veterinary composition comprising a Formula (1) compound, Formula (1.1) compound, or Compound A, in combination with b) a macrocyclic lactone or derivative thereof, and optionally, c) at least one additional veterinary agent. The composition further comprises at least one pharmaceutical or veterinary acceptable carriers. The amount of the compound of the present invention that is administered and the dosage regimen for treating a condition or disorder with the compound depends on a variety of factors, including the age, weight, sex and medical condition of the animal, the severity of the disease, the route and frequency of administration, and thus may vary widely. It is preferable for the administration of the composition of the present invention to be administered concomitantly and preferably simultaneously. However, the composition can also be administered sequentially, for example, separate compositions in a dual tube configuration that are freely mixed upon administration.

Administration of the composition of the present invention is contemplated to be once a month. However, an extended duration formulation may allow for dosing once every 2, 3, 4, 5, or 6 months. A once a year dose is also contemplated.

Preferably, administration of the composition of the instant invention is carried out so as to administer to the animal a dose of a Formula (1) compound, Formula (1.1) compound, or Compound A, ranging from about 0.1 to 25 mg/kg, preferably from about 0.5 to 10 mg/kg, and even more preferably from about 1 to 5 mg/kg, and most preferably from about 1 to 2.5 mg/kg. For the additional veterinary agents, for example, pyrantel, fenbendazole, ivermectin, selamectin, moxidectin, milbemycin oxime, oxantel, imidacloprid, and the like, dose ranges will generally range in accordance with approved product labels. For example, a dose range of about 0.5 to 10 µg/kg for moxidectin is contemplated. More preferred, a moxidectin dose range of about 1 to 5 µg/kg, and more preferably, about 3 µg/kg is contemplated. An approved dose of milbemycin oxime (0.5 to 2 mg/kg), (0.6 µg/kg), and selamectin (6 mg/kg), is contemplated.

In another instance, a dose range of about 1 to 15 mg/kg is contemplated for pyrantel. More preferred, a pyrantel dose of about 2 to 10 mg/kg, or more preferably 5 mg/kg is contemplated. Further, approved doses for the additional veterinary agent(s) include, for example, imidacloprid (10 mg/kg), febantel (15 mg/kg), praziquantel (3.5 to 12 mg/kg), oxantel (20 mg/kg), piperazine citrate (200 mg/kg), and lufenuron (10 mg/kg), are contemplated. For a topical solution, the range of a Formula (1) compound, Formula (1.1) compound, or Compound A, is about 0.1 to 1000 mg/mL, and preferably from about 0.5 to 500 mg/mL, and more preferably from about 1 to 250 mg/mL, and even more preferably from about 2 to 200 mg/mL. Depending upon the final volumes of the topical solution(s), the concentration of the actives can change from that described above. Similarly, the macrocyclic lactone and derivatives thereof, as well as the additional veterinary agents are generally dosed in an amount comparable to the approved dose for said compound.

For an injectable composition, lower doses of a Formula (1) compound, Formula (1.1) compound, or Compound A may require lower amounts versus those administered in an oral or topical composition. Similarly, the additional veterinary agent(s) and the macrocyclic lactone and or derivatives thereof, may also require dosing changes.

Suitable pharmaceutical or veterinary acceptable carriers are well known to those skilled in the art and include materials such as carbohydrates, waxes, water soluble and/or swellable polymers, hydrophilic or hydrophobic materials, gelatin, oils, solvents, water, and the like. The particular carrier will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the composition or aid in the manufacturing of the composition.

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). The composition of the present invention is typically formulated into veterinary dosage forms to provide an easily controllable dosage form for administration. Further, a Formula (1) compound, Formula (1.1) compound, or Compound A can be formulated into a spray dried dispersion prior to being added to the final dosage form.

The choice of carrier will to a large extent depend on factors such as the particular mode of administration, the effect of the carrier on solubility and stability, and the nature of the dosage form.

The methods by which the composition of the present invention may be administered include oral, topical, and injectable.

The composition of the present invention can be administered orally by capsule, bolus, tablet, powders, lozenges, chews (hard and soft palatable), multi and nanoparticulates, gels, solid solution, films, sprays, or liquid form. Oral administration is a preferred method for administering the composition. An oral formulation further comprises at least one carrier, for example, water, ethanol, polyethylene glycol, N-methylpyrrolidone or other pyrrolidones, gelatinized and pre-gelatinized starch, propylene glycol, glycerol, sodium starch glycolate, methylcellulose, sugars (lactose, dextrose, mannose, and the like) or a suitable vegetable oil, and one or more emulsifying agents, flavorants (for example, animal (pork, beef, swine) and non-animal flavorants (smoke, and other synthetic flavorants), and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the compound of the present invention in a suitable medium (e.g. triethylene glycol, benzyl alcohol, and the like). The composition of the present invention can also be formulated with a food substance, e.g., a dietary admixture (food pellets for birds and fish). Preservatives and antioxidants can also be included in the formulations (for example, sodium benzoate, butylated hydroxyanisole (BHA), butylated hydroxytoluene (BHT), citric acid, and the like).

The composition of the present invention can also be administered topically to the skin or mucosa, that is dermally or transdermally. This is another preferred method of administration and as such it is desirable to develop the composition of the present invention to be suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used as a carrier. Typical carriers include alcohol, water, mineral oil, liquid petrolatum, white petrolatum, glycerin, N-methyl formamide, mono and diglycol ethers (for example, diethyleneglycol monomethyl ether (DEGMME) diethyleneglycol monoethylether (DEGMEE), and the like), polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the active agents within the composition of the present invention have increased persistence of action and is more durable, for example it may be more water-fast. Topical formulations contemplated herein can comprise from about 0.1 mg/kg to about 50 mg/kg of a Formula (1) compound, Formula (1.1) compound, or Compound A of the present invention, and more preferably from about 1 mg/kg to about 10 mg/kg, and even more preferably, from about 1 mg/kg to about 5 mg/kg.

The composition of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinary acceptable amount of a Formula (1) compound. Such formulations are prepared in a conventional manner in accordance with standard medicinal or veterinary practice. Further, these formulations will vary with regard to the weight of active compound contained therein, respective salt forms, species of host animal to be treated, the severity and type of infection or infestation, and the body weight of the animal. The volume of the applied composition can be from about 0.2 mL/kg to about 5 mL/kg and preferably from about 1 mL/kg to about 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA).

Certain topical formulations may include unpalatable additives to minimize oral exposure.

Injectable (e.g., subcutaneous and parenteral) formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending a Formula (1) compound, Formula (1.1) compound, Compound A, macrocyclic lactone, or derivative thereof, and optionally, an additional veterinary agent in the liquid carrier such that the final formulation contains from about 0.01 to 30% by weight of the active ingredients.

Suitable devices for injectable administration include needle (including micro needle) injectors, needle-free injectors and infusion techniques. Injectable formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of injectable formulations under sterile conditions, for example, by lyophilisation, may readily be accomplished using standard veterinary techniques well known to those skilled in the art. The solubility of the veterinary parasiticides (i.e., Formula (1) compounds, macrocyclic lactones and derivatives thereof, and additional veterinary agents) used in the preparation of an injectable solution may be increased by the use of appropriate formulation techniques, such as the incorporation of solubility-enhancing agents.

Method of Use

The present invention further comprises methods for treating a parasitic infection and/or parasitic infestation in an animal having or being susceptible to such infection or infestation, by administering to the animal in need thereof, a therapeutically effective amount of a composition of the present invention.

The compound, (S)-1-(5-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (Compound A) is useful as an antiparasitic agent, therefore, another embodiment of the present invention is a veterinary composition comprising a therapeutically effective amount of the compound prepared from the polymorphic Form A of said compound, and a veterinary acceptable carrier. The polymorphic Form A of 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone can also be used in the manufacture of an antiparasitic medicament for the therapeutic applications described herein.

The composition of the present invention is useful as an ectoparasiticide and endoparasiticide that can be used in the fields of veterinary medicine, livestock husbandry and the maintenance of public health: against acarids and insects which are parasitic upon vertebrates, particularly warm-blooded vertebrates, including companion animals, livestock, and fowl. Some non-limiting examples of ectoparasites include: ticks (e.g., *Ixodes* spp., (e.g., *I. ricinus, I. hexagonus*), *Rhipicephalus* spp., (e.g., *R. sanguineus*), *Boophilus* spp., *Amblyomma* spp. (e.g., *A. maculatum, A. triste, A. parvum, A. cajennense, A. ovale, A. oblongoguttatum, A. aureolatum, A. cajennense*), *Hyalomma* spp., *Haemaphysalis* spp., *Dermacentor* spp. (e.g., *D. variabilis, D. andersoni, D. marginatus*), *Ornithodorus* spp., and the like); mites (e.g.,

*Dermanyssus* spp., *Sarcoptes* spp., (e.g., *S. scabiei*), *Psoroptes* spp., (e.g., *P/bovis*), *Otodectes* spp., *Chorioptes* spp., *Demodex* spp., (e.g., *D. folliculorum, D. canis,* and *D. brevis*) and the like); chewing and sucking lice (e.g., *Damalinia* spp., *Linognathus* spp., *Cheyletiella* spp., *Haematopinus* spp., *Solenoptes* spp., *Trichodectes* spp., *Felicola* spp., and the like); fleas (e.g., *Siphonaptera* spp., *Ctenocephalides* spp., and the like); biting flies, midges, and mosquitoes (e.g., *Tabanidae* spp., *Haematobia* spp., *Musca* spp., *Stomoxys* spp., *Dematobia* spp., *Cochliomyia* spp., *Simuliidae* spp., *Ceratopogonidae* spp., *Psychodidae* spp., *Aedes* spp., *Culex* spp., *Anopheles* spp., and the like); bed bugs (e.g., insects within the genus *Cimex* and family Cimicidae); and grubs (e.g., *Hypoderma bovis, H. lineatum*).

The composition of the present invention can also be used for the treatment of endoparasites, for example, heartworms, roundworms, hookworms, whipworms, tapeworms, fluke, and other cestodes and trematodes. The gastrointestinal roundworms include, for example, *Ostertagia ostertagi* (including inhibited larvae), *O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include: hookworms (e.g., *Ancylostoma caninum, A. tubaeforme, A. braziliense, Uncinaria stenocephala*); lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); screw worm (e.g., *Cochliomyia hominivorax* (larvae); filarial nematodes of the super-family Filarioidea and the Onchocercidae Family. Non-limiting examples of filarial nematodes within the Onchocercidae Family include the genus *Brugia* spp. (i.e., *B. malayi, B. pahangi, B. timori,* and the like), *Wuchereria* spp. (i.e., *W. bancrofti*, and the like), *Dirofilaria* spp. (*D. immitis, D. repens, D. ursi, D. tenuis, D. spectans, D. lutrae,* and the like), *Dipetalonema* spp. (i.e., *D. reconditum, D. repens*, and the like), *Onchocerca* spp. (i.e., *O. gibsoni, O. gutturosa, O. volvulus,* and the like), *Elaeophora* spp. (*E. bohmi, E. elaphi, E. poeli, E. sagitta, E. schneideri,* and the like), *Mansonella* spp. (i.e., *M. ozzardi, M. perstans,* and the like), and *Loa* spp. (i.e., *L. loa*). In another aspect of the invention, the composition of the present invention is useful for treating endoparasiticidal infection from filarial nematodes within the genus *Dirofilaria* (i.e., *D. immitis, D. repens, D. ursi, D. tenuis,* and the like).

The compositions of the invention can be administered in a way appropriate to the specific use envisaged, the particular host animal and weight of host animal being treated, the parasite or parasites involved, degree of infestation, etc., according to standard veterinary practice. The veterinary practitioner, or one skilled in the art, will be able to determine the dosage suitable for the particular animal, which may vary with the species, age, weight, and response. The average doses are exemplary of the average case. Accordingly, higher or lower dosage ranges may be warranted, depending upon the above factors, and are within the scope of this invention.

The following list of additional veterinary agents together with which the composition of the present invention can be used is intended to illustrate the possible combinations, but not to impose any limitation. Non-limiting examples of additional veterinary agents include: amitraz, arylpyrazoles, amino acetonitriles, anthelmintics (e.g., albendazole, cambendazole, dichlorvos, fenbendazole, flubendazole, mebendazole, octadepsipeptides, oxantel, oxfendazole, oxibendazole, paraherquamide, parbendazole, piperazines, praziquantel, epsiprantel, thiabendazole, tetramisole, triclabendazole, levamisole, pyrantel, oxantel, morantel, monepantel, and the like), avermectins (e.g., abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., lufenuron, novaluron, hydroprene, kinoprene, methoprene, and the like), metaflumizone, niclosamide, nitenpyram, permethrin, pyrethrins, pyriproxyfen, spinosad, and the like. In certain instances, compositions of the present invention with at least one additional veterinary agent can result in a greater-than-additive effect. Non-limiting examples of combinations include, but are not limited to: a Formula (1) compound, Formula (1.1) compound, or Compound A, with moxidectin and pyrantel pamoate; a Formula (1) compound, Formula (1.1) compound, or Compound A with milbemycin or milbemycin oxime, and pyrantel pamoate or levamisole; Compound A and selamectin; Compound A, moxidectin, and imidacloprid; Compound A, moxidectin, and praziquantel; and the like.

The veterinary composition for application to an animal may be packaged in a variety of ways depending upon the method used for administering the composition of the present invention. Generally, an article for distribution includes a container having deposited therein the veterinary composition in an appropriate form. Suitable containers are well-known to those skilled in the art and include materials such as bottles (plastic and glass), sachets, ampoules, blister-paks, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

EXAMPLES

Example 1

Antiparasitic Composition Comprising: Compound A (2 mg/kg), moxidectin (3 µg/kg), and pyrantel (5 mg/kg), and optionally, at least one veterinary acceptable carrier.

Example 2

Antiparasitic Composition Comprising: Compound A (2 mg/kg), milbemycin oxime (0.5 mg/kg), and pyrantel (5 mg/kg), and optionally, at least one veterinary acceptable carrier.

Example 3

Antiparasitic Composition Comprising: Compound A (2 mg/kg), ivermectin (6 µg/kg), and pyrantel (5 mg/kg), and optionally, at least one veterinary acceptable carrier.

Example 4

Antiparasitic Composition Comprising: Compound A (2 mg/kg), milbemycin (0.5 mg/kg), and pyrantel (5 mg/kg), and optionally, at least one veterinary acceptable carrier.

Example 5

Antiparasitic Composition Comprising: oxantel in place of pyrantel as described in Examples 1-4, and optionally, at least one veterinary acceptable carrier.

Example 6

Antiparasitic Composition Comprising: morantel in place of pyrantel as described in Examples 1-4, and optionally, at least one veterinary acceptable carrier.

Example 7

Antiparasitic Composition comprising Compound A and selamectin, and optionally, at least one veterinary acceptable carrier.

Example 8

Antiparasitic Composition comprising Compound A and moxidectin, and optionally, at least one veterinary acceptable carrier.

Example 9

Antiparasitic Composition comprising Compound A and milbemycin or milbemycin oxime, and optionally, at least one veterinary acceptable carrier.

Example 10

Antiparasitic Composition comprising Compound A and ivermectin, and optionally, at least one veterinary acceptable carrier.

Biological

In-Vitro Endoparasite Evaluation

The purpose of the experiment was to evaluate concentrations of moxidectin, pyrantel pamoate and Compound A that reduce motility less than 100% alone and then combine selected suboptimal concentrations to gain an understanding of any effect on motility of a susceptible and resistant strain of *Haemonchus contortus* (barber pole worm) L3 and a Michigan strain of heartworm (*Dirofilaria immitis*) microfilariae (MF), in vitro.

Antiparasitic compounds were dissolved in DMSO and were spotted into the well of a 384 well microtiter plate. Nematodes in a buffered solution were added to the plates and motility measured at 96 hours for the *H. contortus* strains and 72 hours for *D. immitis*. Each test compound was assayed individually against each nematode with an 11 point ½ log dose curve from 100 μM to 1 nM and minimum efficacious dose (MED) was determined. MED was subjective based on visual assessment using light microscopy and was the lowest dose to cause a significant decrease in motility. Concentrations at ½ log below the MED were used alone and in combination and were read on the LemnaTec Scanalyzer to provide a quantitative percent motility compared to the negative control. MED data are presented in Table 1.

Material and method for the *Haemonchus contortus* in vitro assay: *H. contortus* L3 were produced from feces of infected sheep and maintained in a buffered nutrient media containing antibiotics. The assay was conducted in a 384 well microtiter plate with a total of 250 nL of DMSO solvated test compound and 25 μl of media containing approximately 100 *H. contortus* L3 per well. The motility assessment was performed after 96 hours of incubation at 37° C. on a LemnaTec Scanalyzer which determined motility of the *H. contortus* L3 by image analysis. The endpoint was defined as percent motility (average/2-plates) compared to that of the untreated control, and is presented in Tables 2 (susceptible) and Table 3 (resistant).

Material and method for the *Dirofilaria immitis* in vitro assay: *Dirofilaria immitis* MF were purified from microfilaremic canine blood by erythrocyte lysis and filtration and maintained in a cell culture media fortified with fetal bovine serum and antibiotics. The assay was conducted in a 384 well microtiter plate with a total of 250 nL of DMSO solvated Compound A and 25 μl of media containing approximately 200 MF per well. The motility assessment was performed after 72 hours of incubation at 37° C. and 5% $CO_2$ on a LemnaTec Scanalyzer which determined motility of the MF by image analysis. The endpoint was defined as percent motility (average/2-plates) compared to that of the untreated control, and is presented in Table 4.

TABLE 1

Individual Compound MED's and Combination Treatments

|  | H. contortus L3 resistant MED μM | H. contortus L3 susceptible MED μM | D. immitis MED μM |
|---|---|---|---|
| Moxidectin | 1 | 0.3 | 10 |
| Pyrantel | 33 | 33 | 100 |
| Compound A | >100 | >100 | 33 |

|  | Final concentration of test combinations | Final concentration of test combinations | Final concentration of test combinations |
|---|---|---|---|
| Treatment 1 | DMSO | DMSO | DMSO |
| Treatment 2 | .3m | .1m | 3.3m |
| Treatment 3 | 10p | 10p | 33p |
| Treatment 4 | 100A | 100A | 10A |
| Treatment 5 | .3m + 10p | .1m + 10p | 3.3m + 33p |
| Treatment 6 | .3m + 100A | .1m + 100A | 3.3m + 10A |
| Treatment 7 | 10p + 100A | 10p + 100A | 33p + 10A |
| Treatment 8 | .3m + 10p + 100A | .1m + 10p + 100A | 3.3m + 33p + 10A | m = moxidectin; p = pyrantel pamoate; A = Compound A.
Numbers = μM dose, for example, .3m + 10p = 0.3 μM moxidectin + 10 μM pyrantel pamoate.

TABLE 2

H. contortus L3 Susceptible Strain

| Dose Amount | % Motility |
|---|---|
| DMSO | 100.0 |
| 0.1 µM Moxidectin | 95.0 |
| 10 µM Pyrantel | 95.6 |
| 100 µM Compound A | 76.0 |
| 0.1 µM Moxidectin + 10 µM Pyrantel | 76.5 |
| 0.1 µM Moxidectin + 100 µM Compound A | 67.0 |
| 10 µM Pyrantel + 100 µM Compound A | 59.5 |
| 0.1 µM Moxi + 10 µM Pyrantel + 100 µM Compound A | 51.8 |

According to the results of the susceptible strain of *H. contortus*, a more than additive effect was observed in reducing larval motility for the moxidectin and pyrantel combination; the Compound A and pyrantel combination; and the Compound A, pyrantel, and moxidectin combination.

TABLE 3

H. contortus L3 Resistant Strain

| Dose Amount | % Motility |
|---|---|
| DMSO | 100.0 |
| 0.3 µM Moxidectin | 64.3 |
| 10 µM Pyrantel | 80.0 |
| 100 µM Compound A | 69.0 |
| 0.3 µM Moxidectin + 10 µM Pyrantel | 43.5 |
| 0.3 µM Moxidectin + 100 µM Compound A | 32.8 |
| 10 µM Pyrantel + 100 µM Compound A | 57.5 |
| 0.3 µM Moxi + 10 µM Pyrantel + 100 µM Compound A | 38.6 |

According to the results of the resistant strain of *H. contortus*, at least a potential additive effect was observed.

TABLE 4

D. immitis Motility

| Dose Amount | % Motility |
|---|---|
| DMSO | 100.0 |
| 3.3 µM Moxidectin | 62.0 |
| 33 µM Pyrantel | 77.8 |
| 10 µM Compound A | 50.9 |
| 3.3 µM Moxidectin + 33 µM Pyrantel | 37.1 |
| 3.3 µM Moxidectin + 10 µM Compound A | 18.1 |
| 33 µM Pyrantel + 10 µM Compound A | 1.7 |
| 3.3 µM Moxi + 33 µM Pyrantel + 100 µM Compound A | 1.3 |

As indicated above, addition of Compound A to either pyrantel or moxidectin resulted in a more than additive, synergistic, effect on *D. immitis* motility.

Efficacy Against *D. immitis* MF and Adult Worms in Dogs

In another study, safety of the triple combination (Compound A, moxidectin, and pyrantel pamoate) was assessed in dogs artificially infected with *D. immitis* MF. Male (7) and female (7) beagle dogs were artificially (surgical transplanted) infected with adult heartworm (10 male and 10 female worms). Three male and 4 female dogs received placebo. Four male and three female dogs received an oral combination (12 mg/kg Compound A, 18 µg/kg moxidectin, and 30 mg/kg pyrantel pamoate) dose on Days 0, 28, & 56. In-life assessments included body weight, directed clinical and neurologic examinations, a qualitative estimate of food intake, and blood collections for pharmacokinetics and serial MF counts. Blood was collected for MF count on Days 0 (pre-dose), 1, 3, 7, 14, 28, 56, and 84. Average blood collected MF are shown in Table 5.

TABLE 5

Average Collected MF

| Day of Study | Placebo | Test |
|---|---|---|
| −14 | 4530 | 3336 |
| 0 | 5699 | 5331 |
| 1 | 6417 | 3836 |
| 3 | 6443 | 3757 |
| 7 | 7174 | 4734 |
| 14 | 10567 | 5714 |
| 28 | 12157 | 6004 |
| 56 | 15129 | 6700 |
| 84 | 20600 | 6950 |

At the end of the study, a partial necropsy (Day 84) was conducted on each dog. The precava, right atrium, right ventricle and pulmonary arteries (including those coursing through the lungs) were dissected and examined for adult worms. The worms from each dog were counted as either alive or dead. Worms that were abnormal in both motility and appearance were considered dead; all others were considered alive. Worm counts from placebo and study animals are presented as an average in Table 6.

TABLE 6

Average Number of Adult *D. immitis* Worms at Necropsy

| | Placebo | Test |
|---|---|---|
| Average number dead males | 0.14 | 0.00 |
| Average number dead females | 0.43 | 0.00 |
| Average number live males | 8.14 | 6.14 |
| Average number live females | 8.29 | 9.29 |

These data indicate that monthly dosing of the combination for 3 months gradually reduces *D. immitis* MF, but does not appear to kill adult heartworms.

Efficacy in the Prevention of Heartworm Disease in Dogs

Dogs were inoculated with 50 infective L3 *D. immitis* larvae on Day −30. On Day 0, dogs (8/group) received either a single oral dose of placebo (T01); Compound A (2 mg/kg), moxidectin (3 µg/kg), and pyrantel pamoate (5 mg/kg) (T02); Compound A (2 mg/kg) (T03); or moxidectin (3 µg/kg) (T04). On Day 120, dogs were humanely euthanized and necropsied for recovery of adult *D. immitis*. The geometric mean adult worm count in the placebo group was 34.2 worms recovered from each dog. No worms were recovered from any dog in the T02 and the T04 groups, resulting in 100% efficacy. Adult *D. immitis* worm counts for T03 were similar to those for the placebo group with a geometric mean of 30.3 worms recovered from each dog. Therefore, a single oral dose of Compound A in combination with moxidectin and pyrantel resulted in 100% efficacy in the prevention of heartworm disease caused by *D. immitis*. Moxidectin alone also provided 100% efficacy, confirming no interference in the efficacy of moxidectin in the combination. Compound A provided virtually no reduction in adult *D. immitis* worm counts relative to placebo.

Efficacy Against Roundworms (*Toxascaris leonina*) in Dogs

Dogs were inoculated with 300 infective *T. leonina* eggs on Day −75. On Day 0, dogs (8/group) received a single oral placebo dose (T01) or Compound A (2 mg/kg) and moxidectin (3 μg/kg), and pyrantel pamoate (5 mg/kg) (T02). On Day 7, dogs were humanely euthanized and necropsied for recovery of adult *T. leonina* worms. Geometric mean adult *T. leonina* worm counts for group T01 was 11.9 worms recovered from each dog. One worm was recovered from one dog in the T02 group, resulting in 99.2% efficacy against adult *T. leonina*. Therefore, a single oral dose of Compound A in combination with moxidectin and pyrantel resulted in 99.2% efficacy in the treatment of adult *T. leonina* infections in dogs. Although the lack of a pyrantel-only group prevents direct comparison to the combination product, these data support a conclusion that neither Compound A nor moxidectin are interfering substantially with the efficacy of pyrantel against adult *T. leonina*.

Efficacy Against Roundworms (*Toxocara canis*) in Dogs

Dogs were inoculated with 300 infective *T. canis* eggs on Day −49. On Day 0, dogs (8/group) received a single oral placebo dose (T01); Compound A (2 mg/kg) and moxidectin (3 μg/kg), and pyrantel pamoate (5 mg/kg) (T02); Compound A (2 mg/kg) (T03); pyrantel (5 mg/kg) (T04); or moxidectin (3 μg/kg) (T05). On Day 7, dogs were humanely euthanized and necropsied for recovery of adult *T. canis* worms. Geometric mean adult *T. canis* worm counts for the placebo group was 11.8 worms recovered from each dog. Geometric mean (range) adult worm counts for T03, T04, and T05 were 8.2, 0.1, and 10.5, respectively. Percentage reduction in worm counts for T02, T03, T04, and T05 groups were 100%, 30.3%, 98.7%, and 10.9%, respectively. Therefore, a single oral dose of Compound A, moxidectin, and pyrantel in combination resulted in 100% efficacy against adult *T. canis*. Similar efficacy was provided by pyrantel alone, confirming no interference with the efficacy of pyrantel in the combination. In this study there was a 30.3% reduction in adult *T. canis* adult worm counts in the T03 group compared to placebo, suggesting Compound A may have some activity against adult *T. canis*. At the dosage evaluated, moxidectin provided virtually no efficacy against *T. canis*.

Efficacy Against Hookworms (*Ancylostoma caninum* and *Uncinaria stenocephala*) in Dogs On Day −29, dogs (8/group) were inoculated with 200 infective *A. caninum* larvae and 400 infective *U. stenocephala* larvae. On Day 0, dogs received a single oral placebo dose (T01) or Compound A (2 mg/kg) and moxidectin (3 μg/kg), and pyrantel pamoate (5 mg/kg) (T02). On Day 7, dogs were humanely euthanized and necropsied for recovery of adult *A. caninum* and *U. stenocephala* worms. Geometric mean adult *A. caninum* worm count for the T01 group was 84.5 worms recovered from each dog. No adult *A. caninum* worms were recovered from any T02 dog, resulting in a 100% efficacy against adult *A. caninum*. Geometric mean adult *U. stenocephala* worm counts for the T01 group were 223.5 worms recovered from each dog. Adult *U. stenocephala* worms were recovered from four of the eight T02 dogs resulted in a geometric mean adult worm count of 1.1 worms recovered from each dog, therefore the efficacy against adult *U. stenocephala* was 99.5%. Therefore, a single oral dose of Compound A in combination with pyrantel and moxidectin resulted in 100% efficacy against adult *A. caninum* and 99.5% efficacy against adult *U. stenocephala*. Although the lack of a pyrantel-only group prevents direct comparison to the combination product, these data support a conclusion that neither Compound A nor moxidectin are interfering substantially with the efficacy of pyrantel against adult *A. caninum* and *U. stenocephala*.

In-Vitro Flea (*Ctenocephalides felis*) Assay

The study was designed to assess sub-lethal concentrations of moxidectin, pyrantel pamoate and Compound A alone and in combination with moxidectin and pyrantel pamoate on flea (*C. felis*) mortality. Fleas were newly emerged (3-7 days) non-fed adults. The assay was an in-vitro flea feeding assay. DMSO solvated compounds were spotted into a 96 well plate, whole blood added to the compounds, and an artificial membrane adhered to the top of the 96 well plate. Fleas were collected into feeding chambers (N=10/well) and placed on top of the compound plate. The fleas fed on the blood meal over a period of 24 hours through the feeding membrane. Each test compound was tested individually in a half dose titration curve from 30 mM to 0.1 mM (moxidectin), and 1 mM to 0.001 mM (Compound A). A minimum efficacious dose (MED) was determined based on these dose titration curves. MED is a subjective visual assessment of organism viability, and is the lowest dose to cause mortality ≥50%. Mortality was compared to that of the untreated control. Pyrantel pamoate had no effect on fleas at the highest dose tested (300 mM).

The lowest MED for Compound A and moxidectin alone was 0.0001 mM and 0.01 mM, respectively. Enhanced activity was observed with an MED being achieved with combined dose levels of Compound A (0.00003 mM) and moxidectin (0.003 μM), suggesting a potential synergistic effect.

To assess the triple combination (i.e., Compound A, moxidectin, and pyrantel pamoate), Compound A was titrated from 0.03 μM to 0.000003 mM; moxidectin was titrated from 0.3 μM to 0.0003 mM; and pyrantel was maintained at a dose of 30 mM. In this assay, the control MED dose levels for Compound A, moxidectin and pyrantel alone were 0.3 mM and 10 mM and >300 mM, respectively. MED was observed at Compound A/moxidectin doses of 0.001/0.003 mM, 0.001/0.001 mM, and 0.000003/0.01 mM. Thus, the addition of pyrantel pamoate does not appear to potentiate the effects beyond that seen with the Compound A/moxidectin combination.

In-Vitro Tick (*Ornithodoros turicata*) Assay

The study was designed to assess sub-lethal concentrations of moxidectin, pyrantel pamoate and Compound A alone and then combined on tick (*O. turicata*, Zoetis strain) in an in-vitro tick feeding assay. DMSO-solvated compounds were spotted into a petri dish, whole blood was added to the compounds, and an artificial membrane was stretched over the top of the plate so that it contacts the blood mixture. Ticks were allowed to feed to repletion (about 15 minutes) and assessed for viability and paralysis over 72 hours A minimum efficacious dose (MED) for moxidectin and Compound A was determined based on dose titration curves. Each test compound was tested individually in a five point half log curve from 3 ug/mL to 0.0003 ug/mL (moxidectin), and 0.1 ug/mL-0.0001 μM (Compound A). MED was based on subjective visual assessment of organism behavior, and is the lowest dose to cause paralysis ≥50% at 24, 28, and 72 hours post feeding. The MED was established for compound A at 0.01 ug/mL and for moxidectin at 0.03 ug/mL. Pyrantel pamoate had no effect at a rate of 3 or 30 ug/mL. There did not appear to be a greater than expected effect on the MED when the test agents were combined versus alone.

Efficacy Against Fleas (*Ctenocephalides felis*) in Dogs

On Day 0, dogs (n=32; 8/group) received either a single oral placebo (T01); Compound A (2 mg/kg), moxidectin (3 μg/kg), and pyrantel pamoate (5 mg/kg) (T02); Compound A (2 mg/kg) (T03); or moxidectin (3 μg/kg) (T04). Each dog was infested with approximately 100 unfed viable adult *C. felis* fleas on Days −1, 6, 13, 20, 27, and 34. Efficacy was assessed by comb counts of live fleas on Days 1, 7, 14, 21, 28, and 35. Efficacy was determined as the % reduction in geometric mean live flea counts versus placebo. Control animals maintained adequate levels of fleas during the study (mean range: 67.9-91.2 fleas per animal per infestation). Results are shown in Table 7.

TABLE 7

In-vivo flea assay

| Day of Study | Group | % Efficacy |
|---|---|---|
| 1 | T01 | NA |
| | T02 | 100 |
| | T03 | 100 |
| | T04 | 0 |
| 7 | T01 | NA |
| | T02 | 100 |
| | T03 | 100 |
| | T04 | 8.7 |
| 14 | T01 | NA |
| | T02 | 100 |
| | T03 | 100 |
| | T04 | 12.0 |
| 21 | T01 | NA |
| | T02 | 100 |
| | T03 | 100 |
| | T04 | 2.8 |
| 28 | T01 | NA |
| | T02 | 100 |
| | T03 | 100 |
| | T04 | 16.1 |
| 35 | T01 | NA |
| | T02 | 100 |
| | T03 | 100 |
| | T04 | 11.3 |

NA—not applicable

Percentage reductions in geometric and arithmetic mean live flea counts compared with placebo were 100% at all time points for T02 and T03 and the geometric mean counts for both of these groups were significantly (P<0.0001) lower than the placebo group at all time points. A single oral dose of Compound A in combination with moxidectin and pyrantel resulted in a 100% efficacy against an existing *C. felis* infestation and against weekly re-infestations of *C. felis* for at least 35 days. Equivalent efficacy was provided by Compound A alone, confirming no interference in the efficacy of Compound A in the combination. Moxidectin provided virtually no reduction in flea counts relative to placebo.

Efficacy Against Ticks (*Ambylomma maculatum*) in Dogs

On Day 0, dogs (n=32; 8/group) received either a single oral placebo (T01); Compound A (2 mg/kg), moxidectin (3 μg/kg), and pyrantel pamoate (5 mg/kg) (T02); Compound A (2 mg/kg) (T03); or moxidectin (3 μg/kg) (T04). Each dog was infested with approximately 50 unfed viable adult *A. maculatum* ticks on Days −2, 5, 12, 19, 26, and 33 and tick counts with removal were conducted on Days 2, 7, 14, 21, 28, and 35. Range was the number of live ticks counted/removed and efficacy was determined as the % reduction in geometric mean live ticks versus placebo. Control animals maintained adequate levels of ticks during the study (mean range: 18.9-23.5 ticks per animal per infestation). Results are shown in Table 8.

TABLE 8

Tick Efficacy

| Day | Group | % Efficacy |
|---|---|---|
| 2 | T01 | NA |
| | T02 | 99.6% |
| | T03 | 99.2% |
| | T04 | 9.2 |
| 7 | T01 | NA |
| | T02 | 100% |
| | T03 | 100% |
| | T04 | 0 |
| 14 | T01 | NA |
| | T02 | 99.3% |
| | T03 | 99.1% |
| | T04 | 0 |
| 21 | T01 | NA |
| | T02 | 99.5% |
| | T03 | 98.7% |
| | T04 | 0 |
| 28 | T01 | NA |
| | T02 | 99.1% |
| | T03 | 100% |
| | T04 | 0 |
| 35 | T01 | NA |
| | T02 | 100% |
| | T03 | 100% |
| | T04 | 0 |

NA—not applicable

A single oral dose of Compound A in combination with moxidectin and pyrantel resulted in >99% efficacy against an existing *A. maculatum* infestation and against weekly re-infestations of *A. maculatum* for at least 35 days. Similar efficacy was provided by Compound A alone, confirming no interference of the efficacy of Compound A in the combination. Moxidectin provided virtually no reduction in tick counts relative to placebo.

Combination Pharmacokinetics

Fed dogs were treated with either a single dose of Compound A (2 mg/kg), moxidectin (0.25 μg/kg), or pyrantel pamoate (5 mg/kg) and then the three compounds were dosed simultaneously. Blood samples were obtained 1 hour post dose and out to 28 days. When dosed alone, Compound A, moxidectin, and pyrantel had AUC (μg·hr/mL) values of 202, 0.562, and 0.671, respectively. When dosed simultaneously, respective AUC values were 206, 0.620, and 0.461. Overall, the compounds appeared to perform comparably when treated as stand-alones versus in combination. No drug related adverse events were noted.

Efficacy Against Fleas and Ticks in Cats: Selamectin Combination

In another combination study, Compound A (1 mg/kg or 2 mg/kg) was topically administered with selamectin (6 mg/kg) to assess the efficacy against *Dermacentor variabilis* and *Ixodes scapularis* ticks and *C. felis* fleas on cats. On Day 0, each treatment group (N=8) received a single topical application: T01 was a placebo control; T02 was Compound A (1 mg/kg) and selamectin; and T03 was Compound A (2 mg/kg) and selamectin). Animals were infested with approximately 50 unfed ticks (approximately equal numbers of females and males) as follows: *D. variabilis*: Days −2, 5, 12, 19, 26, 33, 40 and 47; *I. scapularis*: Day 26. Animals were also infested with ~100 *C. felis* fleas on the following days: Days 13, 27, 41, and 48. Parasite counts were performed 24 hours after each infestation of fleas (Days 14, 28, 42 and 49) and 48 hours after each infestation of ticks (Days: 2, 7, 14, 21, 28, 35, 42 and 49). Efficacy was determined as % reduction in total flea and/or tick count. Results are shown in Table 9.

TABLE 9

Feline Efficacy (% Reduction) Against Fleas and Ticks Following Single topical Applications of the Combination (Compound A and Selamectin)

| | | Day 2 | Day 7 | Day 14 | | Day 21 | Day 28 | | Day 35 | | Day 42 | | Day 49 | |
|---|---|---|---|---|---|---|---|---|---|---|---|---|---|---|
| | | Dv | Dv | Dv | Flea | Dv | Dv | Is | Dv | Flea | Dv | Flea | Dv | Flea |
| T02 | % AM | 89.3 | 99.6 | 96.6 | 100 | 97.0 | 97.1 | 95.9 | 94.9 | 99.4 | 96.9 | 99.8 | 63.5 | 98.7 |
| | % GM | 95.2 | 99.7 | 98.1 | 100 | 97.7 | 96.7 | 96.4 | 96.2 | 99.6 | 98.0 | 99.9 | 80.1 | 99.3 |
| T03 | % AM | 99.2 | 99.2 | 99.0 | 100 | 99.6 | 98.9 | 92.2 | 98.1 | 100 | 97.1 | 100 | 74.5 | 98.2 |
| | % GM | 99.3 | 99.3 | 99.4 | 100 | 99.7 | 99.0 | 95.8 | 98.4 | 100 | 98.9 | 100 | 89.2 | 99.5 |

Dv = *D. variabilis*;
Is = *I. scapularis*;
AM = arithmetic mean;
GM = geometric mean Infestation levels in the control animals were acceptable throughout the study, with a mean range of 16.4 to 33.6 ticks per infestation for *D. variabilis* and 62.6 to 77.5 fleas. The mean infestation level for *I. scapularis* on Day 28 in the control animals was 9.1 ticks. Compound A, in combination with selamectin was highly effective (>95%) against *D. variabilis* ticks for 42 days when dosed as low as 1 mg/kg, when measured by geometric means. Efficacy against *I. scapularis* was only assessed on Day 28 in this study, but the activity against this species was similar to that of *D. variabilis*. Activity against fleas was very robust (>98% for 49 days). Thus, in this study a topical combination containing ≤2 mg/kg of Compound A and selamectin (6 mg/kg) was >95% effective for at least 1 month against both *D. variabilis* and *I. scapularis* ticks and *C. felis* fleas on cats.

Efficacy Against Hookworms and Roundworms in Cats: Selamectin Combination

In yet another combination study, Compound A (2 mg/kg) and selamectin (6 mg/kg) were topically applied to cats artificially infected with adult gastrointestinal nematodes *Ancylostoma tubaeforme* and *Toxocara cati*. Group T01 (control) and T02 (test) animals were inoculated with *T. cati* (roundworm) eggs on Day −60 and *A. tubaeforme* (hookworm) larvae on Day −30. All animals were treated with a single topical application on Day 0. Fecal egg counts were performed on Days −2 and 7 and necropsy for recovery of adult worms was performed on Day 7. Efficacy (% reduction) was determined by assessing fecal egg count and total adult worms. Efficacy results are shown in Table 10.

TABLE 10

Endoparasitic Efficacy of the Combination of Compound A and Selamectin Following a Single Topical Dose in Cats.

| | | Fecal Egg Counts (Day 7) | | Total Adult Worm Counts (Day 7) | |
|---|---|---|---|---|---|
| Group | | *A. tubaeforme* | *T. cati* | *A. tubaeforme* | *T. cati* |
| T02 | % (AM) | 100 | 100 | 100 | 100 |
| | % (GM) | 100 | 100 | 100 | 100 |

AM = arithmetic mean;
GM = geometric mean

The combination, Compound A and selamectin, was 100% effective in eliminating adult infections of both hookworms (*A. tubaeforme*) and roundworms (*T. cati*) in cats following a single topical application.

Overall, the combination of Compound A with moxidectin or selamectin, Compound A with pyrantel, or Compound A with moxidectin or selamectin and pyrantel, were efficacious against endoparasites (barber pole worms, heartworms, hookworms and roundworms) and ectoparasites (fleas and ticks), where in some instances, a more than additive, synergistic, effect was observed.

We claim:
1. A composition comprising a) a Formula (1) compound,

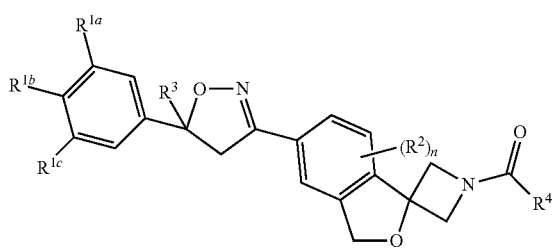

(1)

wherein
R$^{1a}$, R$^{1b}$, and R$^{1c}$ are each independently hydrogen, halo, hydroxyl, cyano, nitro, C$_1$-C$_6$alkyl, C$_1$-C$_6$haloalkyl, C$_1$-C$_6$alkoxy, C$_0$-C$_3$alkylC$_3$-C$_6$cycloalkyl, C$_1$-C$_6$haloalkoxy, —C(O)NH$_2$, —SF$_5$, or —S(O)$_p$R;
R$^2$ is fluoro, chloro, or C$_1$-C$_6$alkyl;
R$^3$ is cyano, C$_1$-C$_6$alkyl, C$_1$-C$_6$haloalkyl, —C(O)NR$^a$R$^b$, C$_2$-C$_6$alkenyl, C$_2$-C$_6$alkynyl, C$_2$-C$_6$haloalkenyl, or C$_2$-C$_6$haloalkynyl
R$^4$ is hydrogen, C$_1$-C$_6$alkyl, C$_2$-C$_6$alkenyl, C$_0$-C$_6$alkylC$_3$-C$_6$cycloalkyl, C$_0$-C$_6$alkylphenyl, C$_0$-C$_6$alkylheteroaryl, or C$_0$-C$_6$alkylheterocycle;
R$^5$ is hydrogen, C$_1$-C$_6$alkyl, hydroxyl, cyano, nitro, —S(O)$_p$R$^c$, or C$_1$-C$_6$alkoxy;
R is C$_1$-C$_6$alkyl or C$_3$-C$_6$cycloalkyl optionally substituted with at least one halo substituent;
R$^a$ is hydrogen, C$_1$-C$_6$alkyl, or C$_0$-C$_3$alkylC$_3$-C$_6$cycloalkyl; wherein the alkyl and alkylcycloalkyl is optionally substituted by cyano or at least one halo substituent;
R$^b$ is hydrogen, C$_1$-C$_6$alkyl, C$_3$-C$_6$cycloalkyl, C$_0$-C$_3$alkylphenyl, C$_0$-C$_3$alkylheteroaryl, or C$_0$-C$_3$alkylheterocycle, each optionally substituted, where chemically possible, with at least one substituent selected from hydroxyl, cyano, halo, or —S(O)$_p$R;
R$^c$ is C$_1$-C$_6$alkyl, C$_1$-C$_6$haloalkyl, C$_1$-C$_6$haloalkylC$_3$-C$_6$cycloalkyl, C$_0$-C$_3$alkylC$_3$-C$_6$cycloalkyl, C$_0$-C$_3$alkylphenyl, C$_0$-C$_3$alkylheteroaryl, or C$_0$-C$_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

when R$^4$ is $C_1$-$C_6$alkyl or $C_0$-$C_6$alkyl$C_3$-$C_6$cycloalkyl, then each moiety can be optionally substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$;

when R$^4$ is $C_0$-$C_6$alkylphenyl, $C_0$-$C_6$alkylheteroaryl, or $C_0$-$C_6$alkylheterocycle, then each moiety can be further optionally substituted with at least one substituent selected from cyano, halo, oxo, =S, =NR$^5$, hydroxyl$C_1$-$C_6$alkyl-, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other; and p is the integer 0, 1, or 2;

stereoisomers thereof, or a pharmaceutical or veterinary acceptable salt thereof;

b) a macrocyclic lactone or derivative thereof, and optionally c) at least one additional veterinary agent.

2. The composition of claim 1 wherein the Formula (1) compound is the S-isomer of the Formula (1.1) compound,

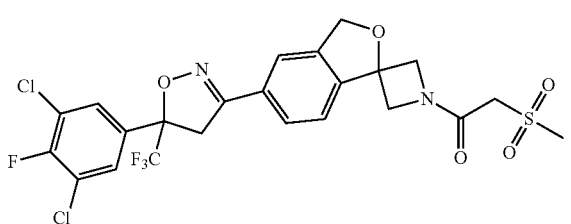

(1.1)

or a pharmaceutical or veterinary acceptable salt thereof.

3. The composition of claim 2, wherein the macrocyclic lactone or derivative thereof is selected from the group consisting of abamectin, eprinomectin, ivermectin, moxidectin, selamectin, doramectin, milbemycin, and milbemycin oxime.

4. The composition of claim 3 further comprising an additional veterinary agent.

5. The composition of claim 4 wherein the additional veterinary agent is selected from the group consisting of pyrantel, oxantel, morantel, imidacloprid, novaluron, febantel, praziquantel, epsiprantel, niclosamide, fenbendazole, oxibendazole, mebendazole, flubendazole, lufenuron, or nitenpyram, or any mixture thereof.

6. The composition of claim 1, further comprising a veterinary or pharmaceutical acceptable carrier.

7. A method of treating a parasitic infection in an animal in need thereof, comprising administering to the animal a therapeutically effective amount of a composition comprising a) the S-isomer of the Formula (1.1) compound,

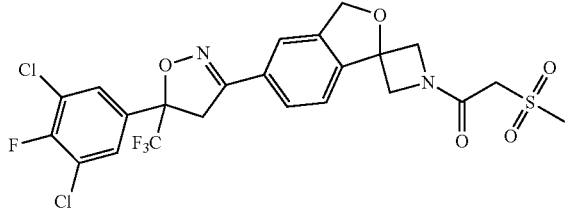

(1.1)

or a pharmaceutical or veterinary acceptable salt thereof; b) a macrocyclic lactone or derivative thereof, and optionally, c) at least one additional veterinary agent.

8. The method of claim 7 wherein the macrocyclic lactone or derivative thereof is selected from the group consisting of abamectin, eprinomectin, ivermectin, moxidectin, selamectin, doramectin, milbemycin, and milbemycin oxime.

9. The method of claim 8 further comprising one additional veterinary agent.

10. The method of claim 9 wherein the additional veterinary agent is selected from the group consisting of pyrantel, oxantel, morantel, imidacloprid, novaluron, febantel, praziquantel, epsiprantel, niclosamide, fenbendazole, oxibendazole, mebendazole, flubendazole, lufenuron, or nitenpyram, or any mixture thereof.

11. The method of claim 7 wherein administration is oral, topical, or by injection.

12. The method of claim 7 wherein the animal is a companion animal or livestock.

13. The composition of claim 3 wherein the macrocyclic lactone or derivative thereof is selected from moxidectin, selamectin, milbemycin, or milbemycin oxime, and further comprises an additional veterinary agent which is pyrantel pamoate.

14. The method of claim 8 wherein the macrocyclic lactone or derivative thereof is selected from moxidectin, selamectin, milbemycin, or milbemycin oxime and further comprising an additional veterinary agent which is pyrantel pamoate.

15. The composition of claim 13 wherein the macrocyclic lactone or derivative thereof is moxidectin.

16. The composition of claim 3 wherein the macrocyclic lactone or derivative thereof is selamectin.

17. The method of claim 8 wherein the macrocyclic lactone or derivative thereof is selamectin and the animal is a companion animal.

18. The method of claim 8 wherein the macrocyclic lactone or derivative thereof is moxidectin and the animal is a companion animal.

19. The method of claim 18 further comprising an additional veterinary agent which is pyrantel and the companion animal is a cat or dog.

20. The method of claim 17 wherein the companion animal is a cat or dog.

* * * * *